United States Patent [19]

Duchon et al.

[11] Patent Number: 5,916,165
[45] Date of Patent: Jun. 29, 1999

[54] PNEUMATIC CONTROLLER AND METHOD

[75] Inventors: Douglas J. Duchon, Chanhassen; James B. Easley, Orono; Christine Kronich, St. Paul, all of Minn.

[73] Assignee: Invasatec, Inc., Eden Prairie, Minn.

[21] Appl. No.: 08/965,583

[22] Filed: Nov. 6, 1997

[51] Int. Cl.[6] .................................................. A61M 5/142
[52] U.S. Cl. ............................ 600/431; 604/181; 604/93
[58] Field of Search ........................... 600/431; 604/181, 604/93, 183, 83, 247, 248, 236

[56] References Cited

U.S. PATENT DOCUMENTS

| | | | |
|---|---|---|---|
| 5,104,387 | 4/1992 | Pokorney et al. | 604/248 |
| 5,336,181 | 8/1994 | Nakao et al. | 604/83 |
| 5,387,188 | 2/1995 | Watson | 604/8 |
| 5,505,707 | 4/1996 | Manzie et al. | 604/131 |
| 5,515,851 | 5/1996 | Goldstein | 128/654 |
| 5,562,617 | 10/1996 | Finch | 604/93 |
| 5,569,208 | 10/1996 | Woelpper et al. | 604/183 |
| 5,573,515 | 11/1996 | Wilson et al. | 604/236 |
| 5,593,385 | 1/1997 | Harrison et al. | 604/83 |
| 5,688,244 | 11/1997 | Lang | 604/118 |
| 5,713,859 | 2/1998 | Finch | 604/93 |
| 5,755,780 | 5/1998 | Finch | 623/1 |

*Primary Examiner*—Marvin M. Lateef
*Assistant Examiner*—Eleni Mantis Mercader
*Attorney, Agent, or Firm*—Oppenheimer Wolff & Donnelly LLP

[57] ABSTRACT

A pneumatic control device includes a housing, a pressure control member secured to the housing, a first fluid-conduit member, and a first sensor. The pressure control member is constructed and arranged to selectively change a fluid pressure within the control member. The first fluid-conduit member is in fluid-flow communication with the pressure control member. The first sensor is in fluid-flow communication with the first fluid-conduit member. The sensor is constructed and arranged to generate a control signal based upon the fluid pressure within the control member. In preferred systems, the pneumatic controller is useful for producing a variable control signal to control a rate of fluid dispersement to a patient in an angiographic system.

40 Claims, 4 Drawing Sheets

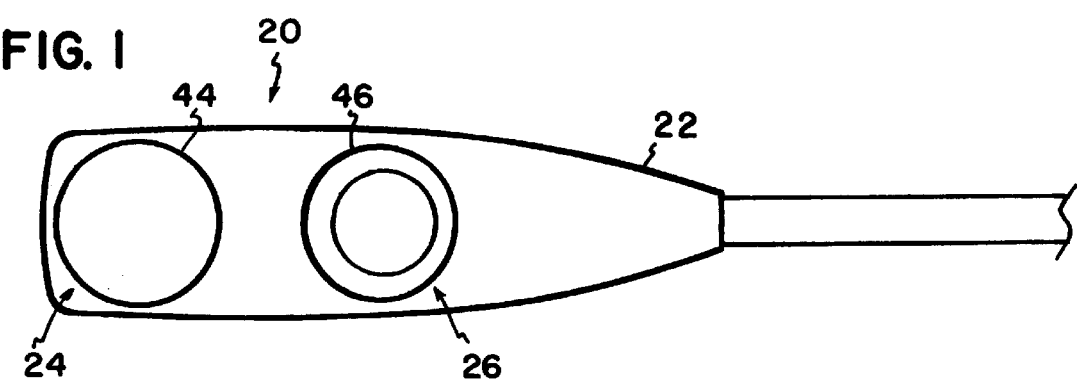
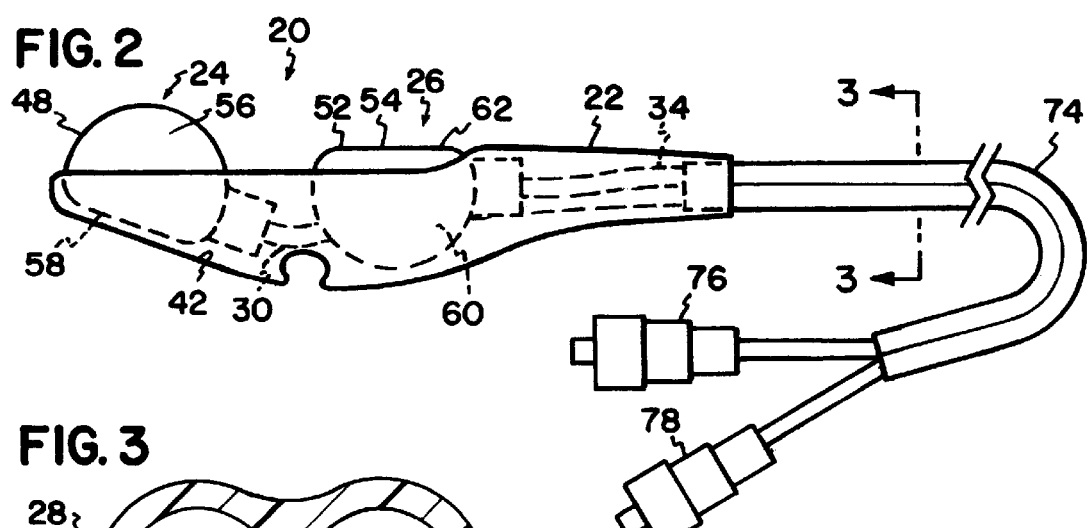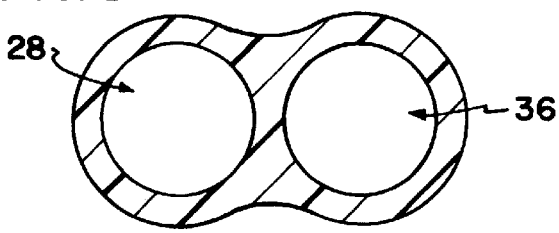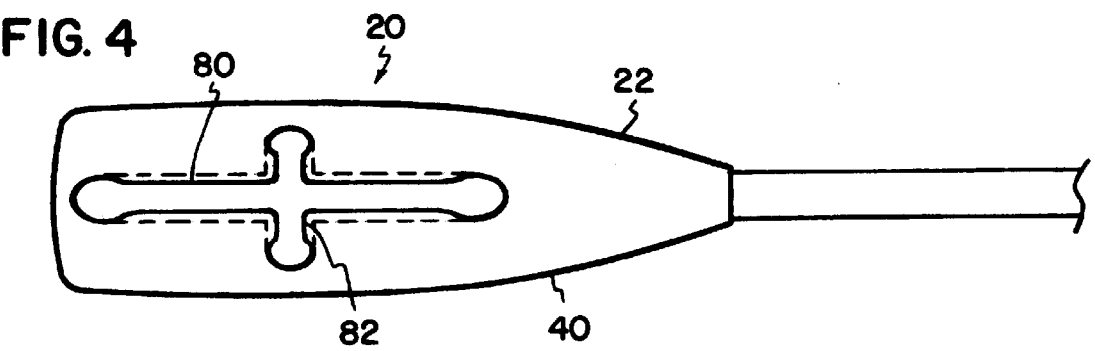

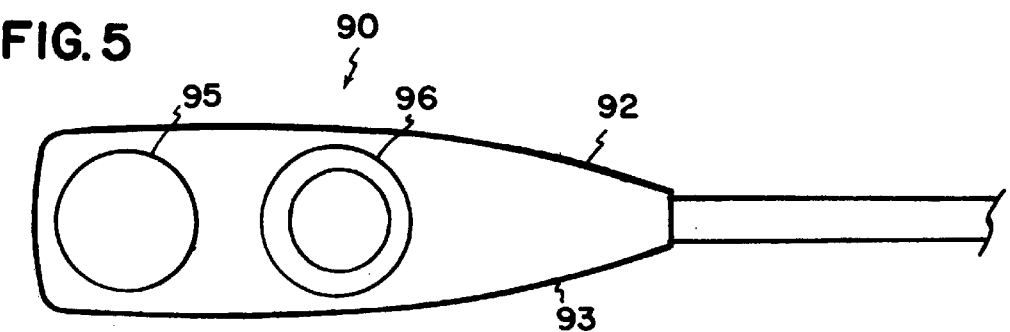
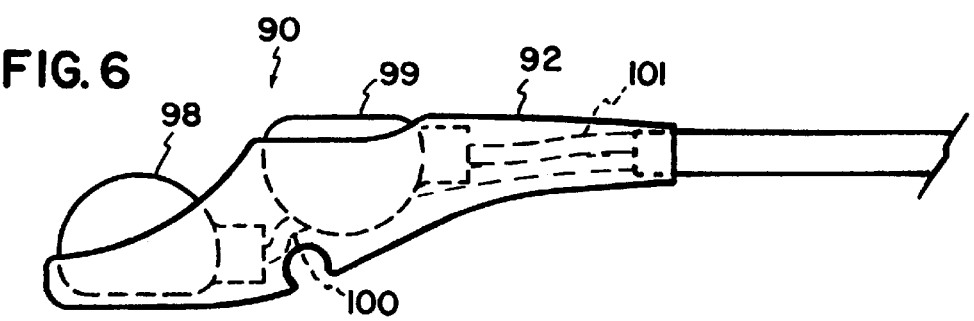
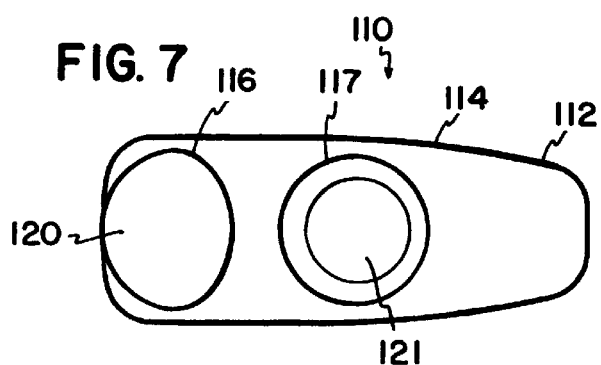
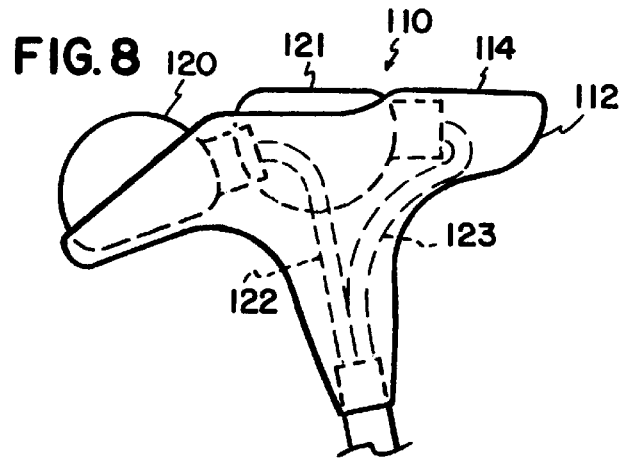

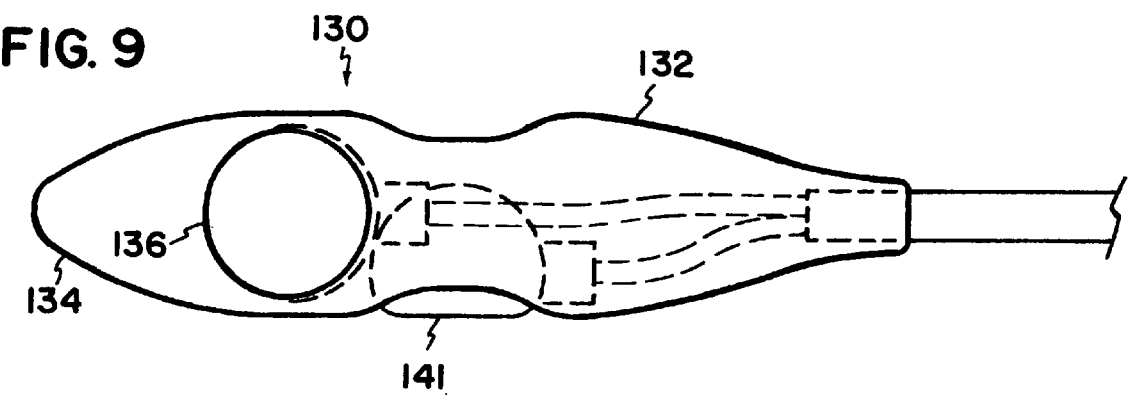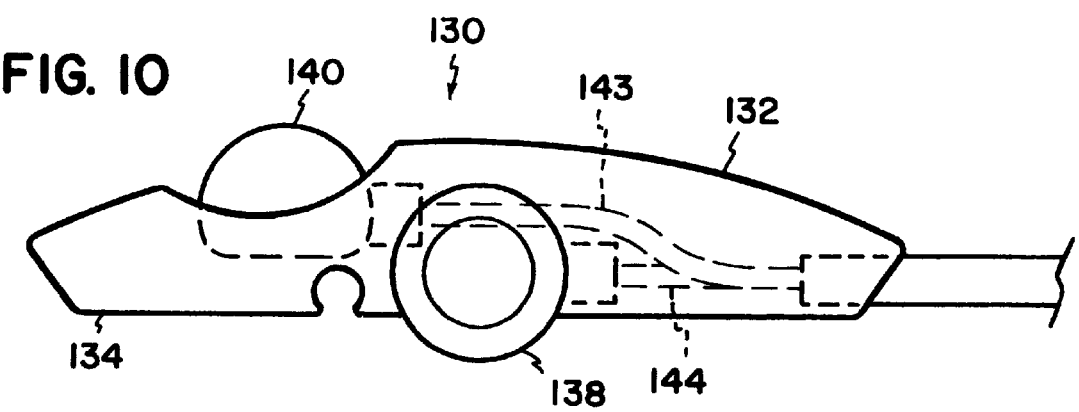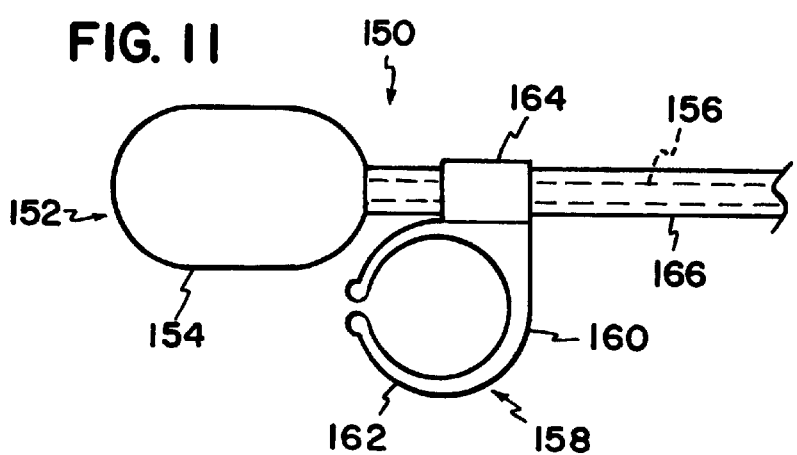

PNEUMATIC CONTROLLER AND METHOD

FIELD OF THE INVENTION

The present invention relates generally to control devices for fluid dispensing machines. In particular, the present invention relates to a pneumatic controller for producing a variable control signal to control fluid dispersement to a patient from an angiographic system.

BACKGROUND OF THE INVENTION

Angiography is a procedure used in the detection and treatment of abnormalities or restrictions in blood vessels. During angiography, a radiographic image of a vascular structure is obtained by injecting radiographic contrast material through a catheter into a vein or artery. The vascular structures fluidly connected with the vein or artery in which the injection occurred are filled with contrast material. X-rays are passed through the region of the body in which the contrast material was injected. The X-rays are absorbed by the contrast material, causing a radiographic outline or image of the blood vessel containing the contrast material. The X-ray's images of the blood vessels filled with the contrast material are usually recorded onto film or video tape and are displayed on a fluoroscope monitor.

During angiography, after a physician places a catheter into a vein or artery, the angiographic catheter is connected to either a manual or an automatic contrast injection mechanism. A typical manual contrast injection mechanism includes a syringe and a catheter connection. The user of the manual contrast injection mechanism adjusts the rate and volume of injection by altering the manual actuation force applied to the plunger of the syringe.

Automatic contrast injection mechanisms typically involve a syringe connected to a linear actuator. The linear actuator is connected to a motor, which is controlled electronically. The operator enters into the electronic control a fixed volume of contrast material and a fixed rate of injection. There is no interactive control between the operator and the machine, except to start or stop the injection. A change in flow rate occurs by stopping the machine and resetting the parameters.

Improvements to controlling an injection mechanism are desirable.

SUMMARY OF THE INVENTION

The present invention is directed to a controlled device to control a fluid supply machine that substantially obviates one or more of the problems due to limitations and disadvantages of the prior art.

To achieve the advantages of the invention and in accordance with the purposes of the invention, as embodied and broadly described herein, the invention comprises a control device for controlling a fluid supply machine. The device includes a housing, a pressure control member secured to the housing, a first fluid-conduit member, and a first sensor. The pressure control member is constructed and arranged to selectively change a fluid pressure within the control member. The first fluid-conduit member is in fluid-flow communication with the pressure control member. The first sensor is in fluid-flow communication with the first fluid-conduit member. The sensor is constructed and arranged to generate a control signal based upon the fluid pressure within the control member.

Preferably, the housing comprises an inexpensive, light weight material. In some preferred applications, the housing is plastic. This permits the housing to be disposable. That is, after using on one patient, the entire housing may be discarded.

Preferably, the housing defines a wall enclosing a housing interior. The pressure control member is positioned within the housing interior.

In some systems, the pressure control member includes a first air bladder oriented within the housing interior and comprising a resilient material. The first air bladder has a volume selectively adjustable to change the fluid pressure within the first air bladder.

In some preferred embodiments, the housing wall defines a first aperture to provide access to the first air bladder. Preferably, a portion of the first air bladder extends through the first aperture, such that it may be controlled by a user.

In one preferred embodiment, the control device includes a second air bladder oriented within the housing interior. The second air bladder has a volume selectively adjustable to change a fluid pressure within the second air bladder. A second fluid-conduit member is in fluid-flow communication with the second air bladder, and a second sensor is in fluid-flow communication with the second fluid-conduit member. The sensor is constructed and arranged to generate a control signal based upon the second air bladder fluid pressure. In some preferred systems, the second air bladder controls dispersement of a saline fluid to a patient.

In one preferred system, the housing defines a second aperture. Preferably, a portion of the second air bladder extends through the second aperture.

In one embodiment, the housing first aperture and second aperture are in a same plane. In another embodiment, the housing first aperture and second aperture are in a pair of parallel planes. In yet another embodiment, the housing first aperture is in a first plane, the housing second aperture is in a second plane; and the first and second planes intersect at an oblique angle. In another embodiment, the housing first aperture is in a first plane, the housing second aperture is in a second plane; and, the second plane is normal to the first plane.

Preferably, the housing defines at least one groove constructed and arranged to snap on to tubing. In certain preferred arrangements, there is a pair of grooves intersecting normal relative to one another. This allows the control device housing to be snap fitted on to any one of a number of tubes in a typical angiographic system.

In certain preferred arrangements, the first air bladder defines a first spherical portion and a first planar portion. The first spherical portion projects through the first aperture in the housing, and the first planar portion is oriented completely within the housing interior. Preferably, in certain embodiments, the second air bladder defines a second spherical portion and a second planar portion. The second planar portion preferably extends through the second aperture, and the second spherical portion is oriented completely within the housing interior. This preferred arrangement provides a different tactical sensation or feel between the first and second air bladders.

In certain preferred embodiments, the first fluid conduit member includes a first flexible lumen, and the second fluid conduit member includes a second flexible lumen. In some preferred embodiments, the first lumen and the second lumen each comprises a plastic tube.

Preferably, the housing is sized to comfortably fit within a user's hand. Preferably, the housing includes a length of no more than about five inches, and a width of no more than about two inches.

In another aspect, the invention is directed to a method for controlling a fluid-supply machine for dispensing fluid into a patient. The method comprises a step of securing a pressure-control member to a fluid-supply machine. A pressure is changed within the pressure-control member by adjusting a volume of the pressure-control member. A fluid is dispensed into a patient, based upon the pressure within the pressure-control member. The steps of changing and dispensing are selectively repeated, until the desired procedure on the patient is completed.

Preferably, after the step of selectively repeating, the pressure control member is removed from the fluid-supply machine. The pressure-control member is then discarded. A new, different, second pressure-control member is then secured to the fluid-supply machine, for operation on a different, second patient.

In one preferred method, the step of securing includes attaching a handpiece which houses the pressure control member. The pressure control member preferably includes a resilient bulb. Preferably, the step of changing includes applying pressure to the bulb. This decreases the volume within the bulb and changes the pressure internal to the bulb.

It is to be understood that both the foregoing general description and the following detailed description are exemplary and explanatory only and are not restrictive of the invention, as claimed.

The accompanying drawings, which are incorporated in and constitute a part of this specification, illustrate example embodiments of the invention and together with the description, serve to explain the principals of the invention.

BRIEF DESCRIPTION OF THE DRAWINGS

FIG. 1 is a top plan view of a first embodiment of a controller, embodying principles of the present invention;

FIG. 2 is a side elevational view of the controller depicted in FIG. 1, embodying principles of the present invention;

FIG. 3 is a cross-sectional view of the section taken along the line 3—3, shown in FIG. 2;

FIG. 4 is a bottom plan view of the controller depicted in FIG. 1;

FIG. 5 is a top plan view of a second embodiment of a controller, embodying principles of the present invention;

FIG. 6 is a side elevational view of the controller depicted in FIG. 5;

FIG. 7 is top plan view of a third embodiment of a controller, embodying principles of the present invention;

FIG. 8 is a side elevational view of the controller depicted in FIG. 7;

FIG. 9 is a top plan view of a fourth embodiment of a controller, embodying principles of the present invention;

FIG. 10 is a side elevational view of the controller depicted in FIG. 8;

FIG. 11 is a top plan view of a fifth embodiment of a controller, embodying principles of the present invention.

DETAILED DESCRIPTION OF THE PREFERRED EMBODIMENTS

Figure 12:
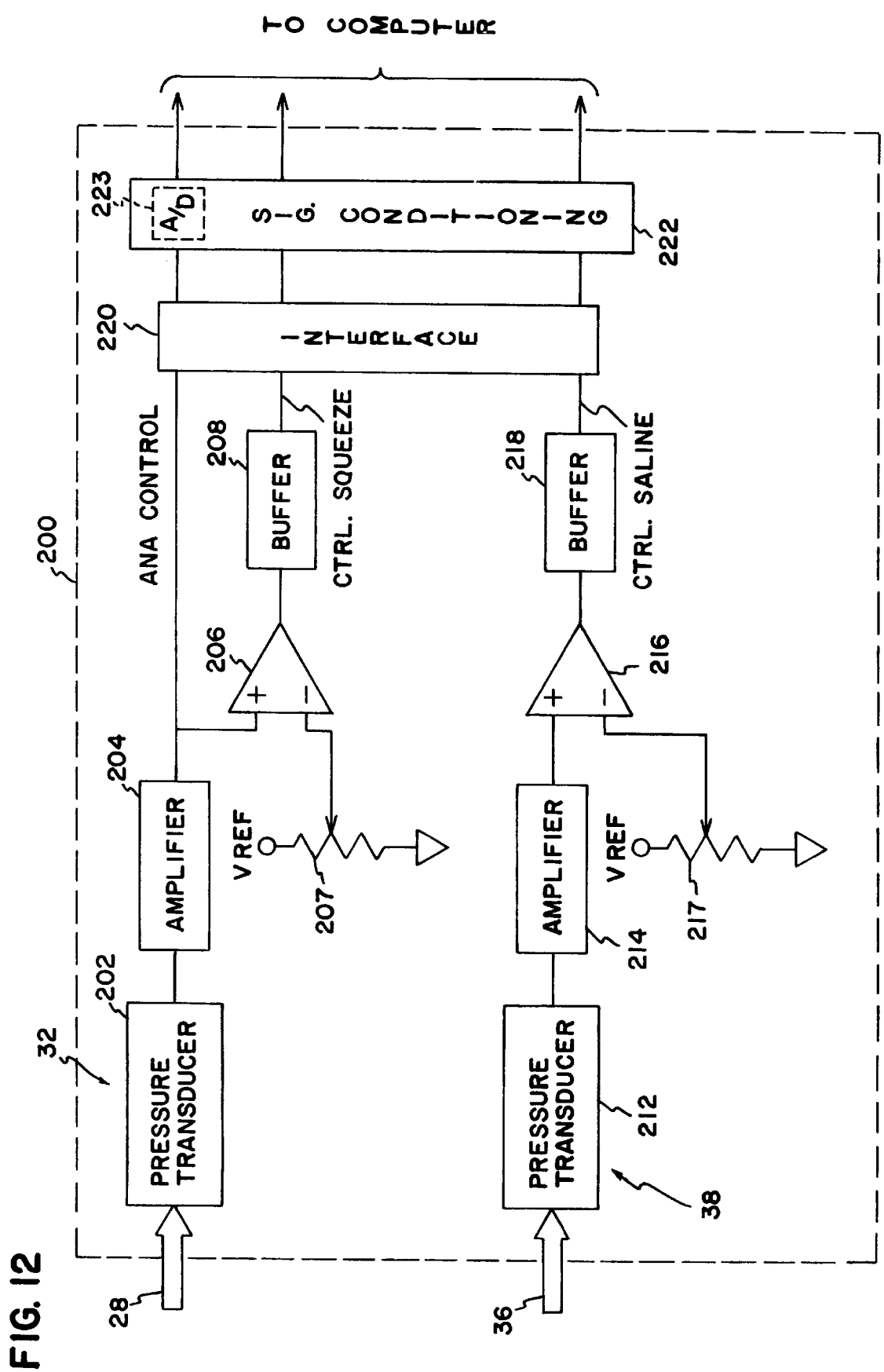
FIG. 12 is a schematic drawing illustrating control aspects of the present invention.

U.S. Pat. No. 5,573,515 to Wilson et al., and commonly assigned as the disclosure herein, describes, among other things, an angiographic injection system which permits the user to control the rate of dispersement of the angiographic fluid through a remote control. The present invention is a pneumatic controller which is usable with the system described in the Wilson et al. patent. Specifically, the present invention produces a variable control signal between a preset maximum value and a minimum value, proportional to the change in air pressure within an air bladder to control the angiographic syringe.

FIGS. 1–4 depict a first embodiment of a control device of the present invention. In FIGS. 1 and 2, a control device is shown generally at 20. Control device 20 includes generally a handpiece or shell or housing 22 which holds and has secured therein at least a single pressure control member 24. The pressure control member is constructed and arranged to selectively change a fluid pressure within the control member, based upon adjustment by a user. In the particular embodiment illustrated in FIGS. 1 and 2, housing 22 holds a second pressure control member 26. Second pressure control member 26 operates analogously to pressure control member 24.

In FIG. 3, a fluid conduit member 28 is in fluid flow, e.g. air-flow or liquid-flow, communication with the pressure control member 24. A fluid pathway 30, FIG. 2, connects the pressure control member 24 to the first fluid conduit member 28. The first fluid conduit member 28 provides a fluid pathway and airflow communication between the pressure control member 24 and first sensor 32 (FIG. 12). First sensor 32 is constructed and arranged to generate a control signal based upon the fluid pressure within the control member 24. That is, first sensor 32 senses a pressure differential between atmospheric pressure and the pressure within the pressure control member 24. Based upon the size of the pressure differential, the first sensor 32 generates a control signal proportional to this size. The control signal regulates the rate of flow of the fluid being dispensed from the angiographic system.

Analogous to pressure control member 2.4, the second pressure control member 26 is connected to a fluid pathway 34, FIG. 2, which provides a fluid flow (air-flow or liquid-flow) communication between the second pressure control member 26 and a second fluid conduit member 36 (FIG. 3). Second fluid conduit member 36 leads to a second sensor 38 (FIG. 12). Second sensor 38 senses a pressure differential between the atmosphere and the pressure within second pressure control member 26, and generates a signal based upon this. Preferably, the second sensor 38 sends a signal to control dispensement of a second fluid within the angiographic system, such as saline.

With the overall principles of operation in mind, we now turn to more specific details of the preferred embodiments.

Housing 22 is provided to hold and contain the pressure control members 24, 26, and prevent the pressure control members 24, 26 from involuntary or unintentional activation. In certain preferred embodiments, housing 22 is constructed of a light weight, durable material. In the preferred embodiment illustrated, housing 22 is constructed of plastic, i.e., top and bottom injection molded halves (for example, a clamshell type construction). The plastic material is inexpensive, in order to permit single use disposability. That is, after the control device 20 is used once on one patient, the entire control device 20 is discarded and not reused. In other embodiments, housing 22 is constructed of cardboard or Styrofoam.

Housing 22 includes a wall 40. Wall 40 encloses a housing interior 42. The first and second pressure control members 24, 26 are positioned and oriented within housing interior 42. In this way, housing 22 helps to protect first and second pressure control members 24, 26 from accidental or unintentional activation.

Wall 40 defines at least a first aperture 44. First aperture 44 provides a window or access port into housing interior 42. Wall 40 may also, in certain embodiments, define a second aperture 46. Second aperture 46 is analogous to first aperture 44, and provides communication between housing interior 42 and the environment external to housing 22.

In the particular embodiment illustrated in FIGS. 1 and 2, first and second apertures 44, 46 are defined in a single plane. That is, the plane which contains the first aperture 44 is coterminous with the plane which contains second aperture 46.

Preferably, control device 20 is sized to easily fit within and be controlled by a person's hand. In the preferred embodiment illustrated in FIGS. 1 and 2, housing 22 is texturized to aid in gripping, especially for use if the user is wearing a latex surgical glove. The texturization includes Mold Tech 11010, available from Mold Tech of Villa Park, Ill.

Housing 22 is constructed such that it can withstand a force of at least about 20 pounds when squeezed by a person's hand. As shown in FIG. 2, housing 22 is contoured, such that it does not pinch or puncture surgical gloves during use.

In the embodiment illustrated in FIGS. 1 and 2, housing 22 is usable by either a person's right hand or left hand. It is sized to fit and be controlled comfortably within a majority of the population's hand. Specifically, housing 22 has a length of no more than about five inches, preferably 3.5–4.5 inches, and more preferably about 3.8 inches. Housing 22 has a width of no more than about two inches, and preferably about 1 inch. The depth of housing 22 is from about 0.5–1.5 inches, and preferably about 1 inch.

Still referring to FIGS. 1 and 2, as described above, pressure control member 24 acts to selectively change a fluid pressure within control member 24. Based upon the change in pressure within control member 24, first sensor 32 sends a signal to the angiographic system to control the rate of fluid, e.g., contrast media, dispensed into the patient. While a variety of embodiments are contemplated, in the particular embodiment illustrated, pressure control member 24 includes a squeeze bulb, or air filled cavity or bag, or air bladder 48.

First air bladder 48 is constructed of a resilient material, such that it retains its shape, but defines a volume which is selectively adjustable. That is, a user applies force to the external surface of wall 50 of air bladder 48. Responsive to the external force applied on wall 50, the wall 50 moves inwardly toward itself, and the volume within air bladder 48 decreases. As the volume within air bladder 48 decreases, the pressure changes, i.e., it increases. The air pressure is conveyed through fluid pathway 30 and first fluid conduit member 28 to first sensor 32. First sensor 32 detects the pressure differential between the pressure within air bladder 48 and atmospheric pressure. Based upon this pressure differential, sensor 32 sends a signal to the angiographic system to control the flow of contrast media.

Upon release of the external force from wall 50, air bladder 48 resumes its original shape. It is ready to be manipulated again by the user.

Preferably, air bladder 48 is constructed from a flexible material, yet one which is able to retain its original shape. Suitable materials include plastic, latex rubber, or elastomeric material. Air bladder 48 is constructed such that the maximum air pressure created when squeezing air bladder 48 does not exceed the pressure which can be accurately and safely handled by sensors 32, 36. In one preferred embodiment, sensors 32, 36 can accurately handle a maximum pressure of about 30 psi. If alternate sensors are used instead of sensors 32, 36, the maximum air pressure can be changed, based upon the particular sensors used.

Second pressure control member 26 is analogous to pressure control member 24. Specifically, second pressure control member 26, in the particular embodiment illustrated, includes a fluid filled cavity or bag, or squeeze bulb, or air bladder 52. Second air bladder 52 includes a wall 54 responsive to an external force. Wall 54 is constructed of a resilient material, such that it is responsive to external forces and will move internally to adjust and change the internal volume of the second air bladder 52.

As with first air bladder 48, second air bladder 52 has a volume selectively adjustable to change the fluid pressure, e.g. air pressure, within the second air bladder 52. When an external force is applied to wall 54, the volume of second air bladder 52 decreases, which increases the pressure. This pressure is conveyed through fluid pathway 34, through second fluid-conduit member 36, and to second sensor 38. Second sensor 38 detects the pressure differential between the pressure within second air bladder 52 and the atmosphere. Although second sensor 38 could operate analogously to first sensor 32 and generate a signal proportional to the pressure differential, second sensor 38 is constructed and arranged to operate as a switch, i.e. a digital-type device. When the pressure differential exceeds a certain amount, second sensor 38 sends a signal to the angiographic system which dispenses a second fluid into the patient, such as saline. In other words, when second air bladder 52 is squeezed or depressed a certain amount, e.g., 50% of the total volume of second air bladder 52, it provides a saline flush into the patient.

First and second air bladders 48 and 52 are each constructed to resemble a truncated sphere. That is, first air bladder 48 defines a first spherical portion 56 and a first planar portion 58. Analogously, second air bladder 52 defines a second spherical portion 60 and a second planar portion 62. In profile, as shown in FIG. 2, the first and second air bladders 48, 52 are generally D-shaped. As described in more detail below, this shape is useful for providing the user with information about which air bladder he is manipulating.

As shown in FIGS. 1 and 2, first air bladder 48 includes a portion which extends through the first aperture 44 of the wall 40. Second air bladder 52 includes a portion which extends through the second aperture 46 of the wall 40. In the particular embodiment illustrated, the first and second air bladders, 48, 52 are oriented such that different ones of their surfaces are projecting through their respective apertures. This provides the user with a different external feel and provides him information as to which button he is manipulating, without having to look at the control device 20. In particular, the first spherical portion 56 of the first air bladder 48 projects through the first aperture 44, while the first planar portion 58 is oriented completely within the housing interior 42. The second planar portion 62 of the second air bladder 52 extends and projects through the second aperture 46, while the second spherical portion of the second air bladder 52 is oriented completely within the housing interior 42. Because of the different contour between the first spherical portion 56 and the second planar portion 62, the user will be able to differentiate between the first and second air bladders 48 and 52.

In reference now to FIG. 2, the first and second fluid pathways 30, 34 are illustrated connecting the first and second air bladders 48, 52 to the first and second fluid conduit members 20, 36. In particular, fluid pathway 30 may include a variety of embodiments, e.g. paratubing, plastic luer fittings, plastic hollow tubing, two discrete tubes bonded together, bi-lumen, tri-lumen, multiple-lumen, etc. In the particular illustrated, fluid pathway 30 is a plastic, hollow tube. Analogously, fluid pathway 34 is a plastic hollow tube.

In reference now to FIGS. 2 and 3, first and second fluid conduit members 28, 36 provide a fluid flow pathway from the fluid pathways 30, 34, respectively. In the particular embodiment illustrated, first fluid conduit member 28 includes a single lumen tubing 70. Second fluid conduit member 36 also includes a single lumen tubing 72. Tubings 70, 72 are held by a single, outer tubing or umbilical tubing 74. Umbilical tubing 74 is flexible, although semirigid, to prevent kinking and blockage of airflow through each lumen 70, 72. . Preferably, the conduit members 28, 36 have sufficient flexibility for ease and comfort of use, yet minimum compliance for better transfer of air pressure. In one preferred arrangement, umbilical tubing 74 withstands a crushing force of about 20 psi without collapsing either of the lumens 70, 72.

In an alternate embodiment, first and second fluid conduit members 28, 36 are rigid channels, columns, or tubes.

Preferably, umbilical tubing 74 is long enough to provide the user with flexibility and movement during angiographic procedures. In the embodiment illustrated in FIG. 2, umbilical tubing 74 is about six feet in length.

In reference now to FIG. 2, umbilical tubing 74 is provided with connectors to connect the lumens 70, 72 to the appropriate air line, and sensor. While a variety of embodiments are contemplated, the FIG. 2 embodiment shows plastic bore fittings or connectors 76, 78. Preferably, connectors 76 and 78 are opposite to each other, such that the user will not be able to mix up the connections. That is, a male luer fitting connects the control line from the first air bladder (which controls the flow of contrast media) to its respective first sensor 32, while a female luer fitting connects the control line from the second air bladder 52 (which controls saline dispensement).

In accordance with the invention, control device 20 may be conveniently stored or oriented in a position with the angiographic system, when not in immediate use. In reference to FIG. 4, control device 20 includes structure which permits control device 20 to be received, hooked by, or snapped into reciprocal structure. The FIG. 4 embodiment shows at least one channel, trench, or groove 80 constructed and arranged to snap on to reciprocal, mating structure, such as tubing. A second groove 82 intersects and is normal to first groove 80. Grooves 80, 82 are defined by and embedded within wall 40 of housing 22. Grooves 80, 82 allow housing 22 to be hooked on or snapped into place in a diverse number of orientations on a number of different tubes in the angiographic system.

As can be appreciated from the foregoing description, at least because, in certain preferred embodiments, control device 20 consists essentially of only housing 22; first and second air bladder 48, 52; first and second fluid pathways 30, 34; and tubing 70, 72, 74, the device 20 is readily disposable. That is, for example, control device 20 is inexpensive to manufacture, and due to the lack of significant extra or expensive components, or electronic components, can be disposed of after using on only one patient. For example, the handpiece lacks any active sensors and magnets. This contributes to cleaner, more sterile, and healthy conditions.

In reference now to FIGS. 5–6, a second embodiment of a control device 90 is illustrated. Control device 90 includes a handpiece or housing 92 having a wall 93. Wall 93 defines first and second apertures 95, 96. In this embodiment, apertures 95, 96 are oriented in two different planes, generally parallel relative to each other, FIG. 6. In addition, as shown in FIG. 5, apertures 95, 96 are non-axially aligned. That is, the center of aperture 95 does not align linearly with the center of aperture 96. A central axis passing through the center of aperture 95 is parallel to a control axis passing through the center of aperture 96.

Control device 90 includes first and second air bladders 98, 99. Air bladders 98, 99 are in fluid flow communication with airflow conduits 100, 101, which lead to sensors, such as those illustrated in FIG. 12.

Control device 90 operates analogously to control device 20. The first and second air bladders 98, 99 are oriented relative to each other differently than in the FIGS. 1–3 embodiment. The FIGS. 5–6 embodiment may, in certain circumstances, be preferred to a user due to the different configuration and arrangement of the air bladders.

FIGS. 7–8 illustrated another embodiment of a control device 110. Control device 110 includes a handpiece or housing 112 including a wall 114. Wall 114 defines first and second apertures 116, 117. In this embodiment, first aperture 116 is contained and defined in a first plane, and second aperture 117 is defined and contained in a second plane. As shown in FIG. 8, the first and second planes intersect at an oblique angle. Specifically, in this embodiment, the angle between the two planes is obtuse, or greater than 90°. A central axis passing through the center of aperture 116, and a central axis passing through the center of aperture 117 intersect at a point in space.

Control device 110 operates analogously to control device 20 and control device 90. Control device 110 includes first and second air bladders 120, 121, and first and second airflow conduits 122, 123. Airflow conduits 122, 123 provide fluid flow communication between air bladders 120, 121 and sensors, such as those illustrated in FIG. 12.

Attention is now directed to FIGS. 9 and 10. In FIGS. 9 and 10, a control device 130 is illustrated. Control device 130 includes a handpiece or housing 132 having a wall 134. Wall 134 defines a first aperture 136, FIG. 9, and a second aperture 138, FIG. 10. In this embodiment, first aperture 136 is defined or contained within a first plane, while second aperture 138 is contained or defined in a second plane normal to the first plane. That is, the second plane is perpendicular to the first plane. A central axis passing through aperture 136 and a central axis passing through aperture 138 are not parallel and do not intersect with each other in space.

Control device 130 operates analogously to control device 20. Control device 130 includes first and second air bladders 140, 141, and first and second airflow conduits 143, 144. First and second air bladders 140, 141 are in fluid flow, i.e. airflow communication with sensors, such as those depicted in FIG. 12.

The arrangement of first and second air bladders 140, 141 relative to one another may be preferred to certain users for comfort and convenience.

Attention is now directed to FIG. 11. In FIG. 11, a control device 150 is illustrated. Control device 150 is devoid of any housing or handpiece. Control device 150 includes a pressure control member 152, and in the particular embodiment illustrated, an air bladder 154. Air bladder 154 is in airflow communication with a fluid conduit member 156. Fluid conduit member 156 is in airflow communication with a first sensor such as sensor 32, illustrated in FIG. 12. Control device 150 operates analogously to control device 20. That is, upon squeezing air bladder 154, the internal volume decreases, increasing the air pressure therein. Sensor 32 detects the pressure differential, and sends a signal to the angiographic system to control the rate of outflow of fluid, such as contrast media.

In the FIG. 11 embodiment, there is illustrated an optional securement member 158. Securement member 158 functions to selectively securably attach or fix control member 152 to an operator's hand. While a variety of working embodiments are contemplated, in the particular embodiment illustrated, securement member 158 is a split ring 160. Ring 160 includes an arcuate portion 162, extending almost a full circle. In the embodiment illustrated arcuate portion 162 extends between about 320°–355°. In other embodiments, arcuate portion 162 extends a full 360°. Ring 160 is constructed of a rigid, yet flexible material. In combination with arcuate portion 162, ring 160 is adjustable between users. Arcuate portion 162 is sized to accommodate a user's finger. In other embodiments, arcuate portion 162 is sized to accommodate other body members.

Connected to arcuate portion 162 is a sleeve 164. Sleeve 164 accommodates and holds umbilical tube 166. Sleeve 164 is sized to slidably accommodate umbilical tube 166, such that control device 150 may be manipulated for comfort and convenience, depending upon the user's preferences and relative size.

The FIG. 11 embodiment is used by sliding a user's finger into arcuate portion 162. Air bladder 154 is held against the palm of the user's hand. When the user desires to inject fluid in an angiographic system, the user depresses air bladder 154 between his finger (or fingers) and the palm of his hand.

Although shown in FIG. 11 with a securement member 158, the securement member 158 is optional. That is, fluid in the angiographic system may be controlled simply by manipulating the air bladder 154. No securement member 158 is required; although, in the FIG. 11 embodiment, it is convenient and preferred.

Attention is now directed to FIG. 12. In general, the control device 20 is operatively connected to a hand-controller circuit functional block 200 that converts the pneumatic pressure from first fluid conduit member 28 and from second fluid conduit member 36 into electrical output signals that are fed back to a computer for processing. The computer is described in U.S. Pat. No. 5,573,515, hereby incorporated by reference.

The hand controller circuit 200 generates three primary signals from the input fluid conduit members 28, 36, respectively. They are: an ANA CONTROL signal, a CTRL SQUEEZE signal and a CTRL SALINE signal. The ANA CONTROL signal represents a 1:1 linear relationship between user pressure (0–100%) on the first air bladder 48 and an analog voltage from 0–5 volts The CTRL SQUEEZE signal is a digital signal indicating that the first air bladder 48 has been depressed 10% of its maximum depression capacity. The CTRL SALINE signal is a digital signal which indicates that the second air bladder 52 has been depressed to 50% of its maximum depression capacity.

Referring to FIG. 12, a diagrammatic block diagram is illustrated that shows the general circuit components of the preferred embodiment used for converting the pneumatic input signals from fluid conduit members 28, 36 to the ANA CONTROL, CTRL SQUEEZE and CTRL SALINE signals used by the computer. Referring thereto, the first fluid conduit member 28 is operatively connected to first sensor 32. In this particular embodiment, first sensor 32 includes a first pressure transducer 202 within the hand controller circuit 200. The first pressure transducer 202 senses the user's contrast flow rate, which is proportional to the hand bulb pressure in the first fluid conduit member 28. As the pressure in first fluid conduit member 28 increases, the pressure transducer 202 produces an electrical output signal that increases proportionately, in a linear manner, with the pressure in the input fluid conduit member 28. The output of the first pressure transducer 202 is fed through an amplifier 204 that converts and amplifies the differential signal to a 0–5 volt analog signal. In its unconditioned form, this signal comprises the ANA CONTROL signal. The ANA CONTROL signal is fed through an Interface network, generally indicated at 220, where it is amplified, conditioned, buffered and filtered. In the preferred embodiment, the conditioned ANA CONTROL signal then passes through a further signal conditioning step, generally indicated by the signal conditioning functional block 222, where the signal passes through an instrumentation amplifier with software selectable gain, and an analog multiplexor and into a 12-bit A/D converter (generally indicated at 223). The output of the A/D converter is fed directly to a computer. The computer controls the flow rate of the contrast injection by adjusting the power applied to the actuator as a user presses and releases the first air bladder 48. In the preferred embodiment, the computer reads the ANA CONTROL signal every ten milliseconds to determine the drive adjustments needed to the actuator for effecting the proper flow rate.

The ANA CONTROL signal from amplifier 204 is also fed to a comparator 206 with an adjustable offset (adjusted by potentiometer 207). The first air bladder 48 can be pressed from 0–100% of its depression capacity. The offset of comparator 206 is adjusted with the bulb pressed to approximately 10% of its full range, such that the comparator provides an output signal when the 10% threshold has been attained. The output of the comparator 206 is buffered by a pair of invertors, generally indicated by the buffer functional block 208 to provide the CTRL SQUEEZE signal, which is a 0–5 volt digital signal. The CTRL SQUEEZE signal is conditioned and buffered by means of circuits within the Interface functional block 220 and is further buffered by a bus buffer within the signal conditioning functional block 222, after which it is fed directly into a register of the computer, which directly reads this user signal.

As the user presses second air bladder 52, the pressure in the second fluid conduit member 36 increases and is applied to second sensor 38; in the particular embodiment illustrated, a second pressure transducer 212. Second pressure transducer 212 converts the pneumatic input pressure in second fluid conduit member 36 to an electrical output voltage, according to a direct linear relationship. The second pressure transducer 212 senses the user's saline injection (start/stop). The output signal from the transducer 212 is fed into an instrumentation amplifier 214 which provides a 0–5 volt analog output signal that is fed to a first signal input of a comparator 216. Comparator 216 also has an adjustable offset which is set by means of a potentiometer 217. The comparator offset adjustment works similarly to that described with respect to comparator 206, except that the offset is adjusted to trigger the comparator 216 when the second air bladder 52 is pressed to 50% of its full compression. The output of the comparator 216 is buffered by a pair of invertors, generally indicated by the buffer functional block 218 the output of which is the CTRL SALINE signal. The CTRL SALINE signal is conditioned and buffered by appropriate circuits within the interface network 220 which is further buffered by a bus buffer within the signal conditioning functional block 222, and is then fed directly into the computer. The computer directly reads the CTRL SALINE signal to start and stop the saline injection, as described in the Wilson, et al. patent.

Other embodiments of the invention will be apparent to those skilled in the art from consideration of the specification and practice of the invention disclosed herein. It is intended that the specification and examples be considered as exemplary only.

We claim:

1. A control device for controlling a fluid-supply machine; the device comprising:
   (a) a housing;
   (b) a pressure control member secured to said housing; said pressure control member being constructed and arranged to selectively change a fluid pressure within said control member;
   (c) a first fluid-conduit member in fluid-flow communication with said pressure control member; and
   (d) a first sensor in fluid-flow communication with said first fluid-conduit member; said sensor being constructed and arranged to generate a control signal based upon said fluid pressure within said control member.

2. A control device according to claim 1, wherein:
   (a) said housing comprises plastic.

3. A control device according to claim 2, wherein:
   (a) said housing defines a wall enclosing a housing interior;
       (i) said pressure control member being positioned within said housing interior.

4. A control device according to claim 3, wherein:
   (a) said pressure control member includes a first air bladder oriented within said housing interior and comprising a resilient material;
       (i) said first air bladder having a volume selectively adjustable to change the fluid pressure within said first air bladder.

5. A control device according to claim 4, wherein:
   (a) said housing wall defines a first aperture;
       (i) at least a portion of said first air bladder extending through said first aperture.

6. A control device according to claim 5, further including:
   (a) a second air bladder oriented within said housing interior; said second air bladder having a volume selectively adjustable to change a fluid pressure within said second air bladder;
   (b) a second fluid-conduit member in fluid-flow communication with said second air bladder; and
   (c) a second sensor in fluid-flow communication with said second fluid-conduit member; said second sensor being constructed and arranged to generate a control signal based upon the second air bladder fluid pressure.

7. A control device according to claim 6, wherein:
   (a) said housing defines a second aperture;
       (i) a portion of said second air bladder extending through said second aperture.

8. A control device according to claim 7, wherein:
   (a) said housing first aperture and second aperture are in a same plane.

9. A control device according to claim 7, wherein:
   (a) said housing first aperture and second aperture are in a pair of parallel planes.

10. A control device according to claim 7, wherein:
    (a) said housing first aperture is in a first plane; said housing second aperture is in a second plane; said first and second planes intersecting at an oblique angle.

11. A control device according to claim 7, wherein:
    (a) said housing first aperture is in a first plane; said housing second aperture is in a second plane; said second plane being normal to said first plane.

12. A control device according to claim 7, wherein:
    (a) said housing defines at least one groove constructed and arranged to snap onto tubing.

13. A control device according to claim 7, wherein:
    (a) said first air bladder defines a first spherical portion and a first planar portion;
        (i) said first spherical portion projecting through said first aperture, and said first planar portion being oriented completely within said housing interior;
    (b) said second air bladder defining a second spherical portion and a second planar portion;
        (i) said second planar portion extending through said second aperture, and said second spherical portion being oriented completely within said housing interior.

14. A control device according to claim 13, wherein:
    (a) said first air bladder is constructed and arranged to cause a force of no greater than about 30 psi, when selectively adjusting volume of the first air bladder; and
    (b) said second air bladder is constructed and arranged to cause a force of no greater than about 30 psi, when selectively adjusting volume of the second air bladder.

15. A control device according to claim 14, wherein:
    (a) said first fluid conduit member includes a first flexible lumen; and
    (b) said second fluid conduit member includes a second flexible lumen.

16. A control device according to claim 15, further including:
    (a) said first and second flexible lumens comprise plastic tubing.

17. A control device according to claim 16, wherein:
    (a) said housing includes a length no more than about 5 inches, and a width no more than about 2 inches.

18. A method for controlling a fluid-supply machine for dispensing fluid into a patient, the method comprising steps of:
    (a) securing a pressure-control member to a fluid-supply machine;
    (b) changing a pressure within the pressure-control member by adjusting a volume of the pressure-control member;
    (c) dispensing a fluid into a patient, based upon the pressure within the pressure control member; and
    (d) selectively repeating said steps of changing and dispensing.

19. A method according to claim 18, further including:
    (a) after said step of selectively repeating, removing the pressure control member from the fluid-supply machine;
    (b) disposing of the pressure-control member; and
    (c) securing a second pressure-control member to the fluid-supply machine.

20. A method according to claim 18, wherein:
(a) said step of securing includes attaching a handpiece housing the pressure control member; the pressure control member including a resilient bulb; and
(b) said step of changing includes applying pressure to the bulb.

21. An angiographic system comprising:
a syringe for holding contrast media;
a plunger movable within said syringe to dispense said contrast media from said syringe;
a motor for moving said plunger;
a controller for said motor;
said controller including a deformable fluid chamber and a pressure sensor, said fluid chamber being in fluid communication with said pressure sensor;
said pressure sensor containing a converter that generates an electrical signal used to set an output of said motor in response to deformation of said fluid chamber.

22. An angiographic system according to claim 21, wherein said fluid chamber is an air chamber.

23. An angiographic system according to claim to claim 21, wherein said controller further includes a hand held housing in which said fluid chamber is disposed.

24. An angiographic system according to claim 23, wherein said controller includes a fluid tube connecting said fluid chamber to said pressure sensor.

25. An angiographic system according to claim 21, wherein said fluid chamber is continuously deformable by a user such that said sensor generates a continuously variable electrical signal.

26. An angiographic system according to claim 21, wherein said system further comprises a second motor for providing one of a saline fluid pumping and a patient fluid aspiration function to said system.

27. An angiographic system according to claim 26, wherein said system further comprises a second deformable fluid chamber and a second pressure sensor, said second fluid chamber being in fluid communication with said second pressure sensor; said second pressure sensor containing a converter that generates an electrical signal used to set an output of said second motor in response to deformation of said second fluid chamber.

28. An angiographic system according to claim 27, wherein said controller includes a comparator for comparing said electrical signal from said second pressure sensor to a threshold value such that said second motor is energized when said electrical signal exceeds said threshold value.

29. An angiographic system comprising:
a container for holding contrast media;
a dispenser device for urging contrast media out of said container;
a controller for said dispenser;
said controller including a deformable fluid chamber and a pressure sensor, said fluid chamber being in fluid communication with said pressure sensor;
said pressure sensor containing a converter that generates an electrical signal used to operate said dispenser device in response to deformation of said fluid chamber.

30. An angiographic system according to claim 29, wherein said container is a syringe.

31. An angiographic system according to claim 30, wherein said dispenser device is a plunger disposed in said syringe.

32. An angiographic system according to claim 29, wherein said deformable fluid chamber is a deformable air chamber.

33. An angiographic system according to claim 29, wherein said pressure sensor is a gas pressure sensor.

34. An angiographic system according to claim 29, wherein said controller further includes a hand held housing in which said fluid chamber is disposed.

35. An angiographic system according to claim 29, wherein said controller includes a fluid tube connecting said fluid chamber to said pressure sensor.

36. An angiographic system according to claim 29, wherein said fluid chamber is continuously deformable by a user such that said sensor generates a continuously variable electrical signal.

37. An angiographic system according to claim 29, wherein said dispenser device includes a plunger disposed in said container and a motor for moving said plunger in said container.

38. An angiographic system according to claim 37, wherein said system further comprises a second motor for providing one of a saline fluid pumping and a patient fluid aspiration function to said system.

39. An angiographic system according to claim 38, wherein said system further comprises a second deformable fluid chamber and a second pressure sensor, said second fluid chamber being in fluid communication with said second pressure sensor; said second pressure sensor containing a converter that generates an electrical signal used to set an output of said second motor in response to deformation of said second fluid chamber.

40. An angiographic system according to claim 39, wherein said controller includes a comparator for comparing said electrical signal from said second pressure sensor to a threshold value such that said second motor is energized when said electrical signal exceeds said threshold value.

* * * * *